United States Patent [19]
Buysch et al.

[11] Patent Number: 5,925,791
[45] Date of Patent: Jul. 20, 1999

[54] PROCESS FOR PRODUCING 4-AMINODIPHENYLAMINE

[75] Inventors: Hans-Josef Buysch, Krefeld; Christian Laue, Monheim; Heinrich Königshofen, Bergisch Gladbach; Ulrich Notheis, Dormagen; Pieter Ooms, Krefeld; Ursula Pentling, Duisburg, all of Germany

[73] Assignee: Bayer AG, Leverkusen, Germany

[21] Appl. No.: 09/031,964

[22] Filed: Feb. 27, 1998

[30] Foreign Application Priority Data

Mar. 6, 1997 [DE] Germany ............ 197 09 124

[51] Int. Cl.$^6$ ................................ C07C 209/30
[52] U.S. Cl. ............ 564/416; 564/415; 564/433; 564/434
[58] Field of Search ............ 564/415, 416, 564/433, 434

[56] References Cited

U.S. PATENT DOCUMENTS

| | | |
|---|---|---|
| 4,187,248 | 2/1980 | Merten et al. . |
| 4,187,249 | 2/1980 | Maender et al. . |
| 4,670,595 | 6/1987 | Podder et al. . |
| 5,117,063 | 5/1992 | Stern ........................ 564/398 |
| 5,420,354 | 5/1995 | Malz ........................ 564/423 |
| 5,608,111 | 3/1997 | Stern ........................ 564/398 |
| 5,739,403 | 4/1998 | Reinartz ..................... 564/423 |

FOREIGN PATENT DOCUMENTS

| | | |
|---|---|---|
| 35 01 698 | 7/1986 | Germany . |
| WO 93/24450 | 12/1993 | WIPO . |

OTHER PUBLICATIONS

Kirk–Othmer, Encyclopedia of Chemical Technology, 4$^{th}$ edition, 1992, vol. 3, pp. 424–447, pp. 448–456.

Ullmann's Encyclopedia of Industrial Chemistry, 5$^{th}$ edition, vol. A3, 1985, pp. 91–111.

*Primary Examiner*—Gary Geist
*Assistant Examiner*—Jean F Vollano
*Attorney, Agent, or Firm*—Connolly and Hutz

[57] ABSTRACT

4-aminodiphenylamines are produced by hydrogenating nitrobenzene with hydrogen in the presence of bases containing hydroxide and/or oxide groups and heterogeneous catalysts and in the presence of inert aprotic solvents at temperatures of 0 to 200° C. and pressures of 0.1 to 150 bars.

9 Claims, No Drawings

PROCESS FOR PRODUCING 4-AMINODIPHENYLAMINE

The invention relates to a process for producing 4-aminodiphenylamine (4-ADPA) by hydrogenation of nitrobenzene with hydrogen in the presence of suitable hydrogenation catalysts and suitable bases.

4-ADPA is an important intermediate product for antioxidants and stabilizers in the rubber and polymer industry (Kirk-Othmer, Encyclopedia of Chemical Technology, 4th edition, 1992, vol. 3, pp. 424-447 and pp. 448456; Ullmann's Encyclopedia of Industrial Chemistry, 5th edition, vol. A3, 1985, pp. 91–111).

4-aminodiphenylamine can be produced by different methods. One possibility of producing 4-ADPA is the two-stage (intermediate product 4-nitrodiphenylamine) conversion of aniline and/or aniline derivatives with p-nitrochlorobenzene in the presence of an acid acceptor or a neutralizing agent and optionally in the presence of a catalyst. Production according to this method is described, for example, in DE-A 35 01 698, DE-A 18 56 63, U.S. Pat. Nos. 4,670,595, 4,187,249, 468,333 and 4 187 248. A disadvantage of such a process is that the halide ions which are produced lead to corrosion in reactors and apparatus and must be disposed of at considerable cost. Furthermore, the starting materials, such as p-nitrochloro- benzene and optionally the corresponding formanilide derivatives, must be produced in additional reaction steps.

To avoid such disadvantages, aniline and/or corresponding aniline derivatives have been reacted with nitrobenzene in the presence of tetraalkylammonium hydroxides and in the presence of controlled quantities of protic materials. 4-ADPA was obtained in a satisfactory quantity (see WO 95/00 324 and WO 93/24 450). The disadvantage of these processes, however, is that two different feed products have to be used and the reaction comprises several process steps, which is less economical.

It was therefore desirable to provide a process for producing 4-ADPA which starts from inexpensive nitrobenzene and leads to the desired 4-ADPA in technically usable yields in one reaction step.

The invention therefore provides a process for producing 4-aminodiphenylamine which is characterized in that nitrobenzene is hydrogenated with hydrogen in the presence of bases containing hydroxide and/or oxide groups and heterogeneous catalysts and in the presence of inert aprotic solvents at temperatures of 0 to 200° C. and pressures of 0.1 to 150 bars.

Inorganic bases such as alkali metal hydroxides, alkali metal oxides, alkaline earth metal hydroxides, alkaline earth metal oxides and the corresponding hydroxides and oxides of elements 58 to 71 of the periodic system of elements (according to IUPAC, new) may be considered as bases containing hydroxide and/or oxide groups which are suitable for the process according to the invention. Examples which may be quoted are: the oxides and hydroxides of sodium, potassium, lithium, caesium, magnesium, calcium, barium, lanthanum and/or cerium, particularly the oxides and hydroxides of lithium, sodium, potassium, caesium, with caesium hydroxide being most particularly preferred.

Organic bases such as quaternary alkylammonium hydroxides ($NR_4^+O^-$ with R independently of each other standing for alkyl, aryl or aralkyl with 1 to 7 carbon atoms) may also be considered. Examples which may be quoted are: tetramethylammonium hydroxide, tetraethylammonium hydroxide, tetrapropylammonium hydroxide, tetrabutylammonium hydroxide, methyltributylammonium hydroxide, methyltripropylammonium hydroxide, methyltriethylammonium hydroxide, trimethylbenzylammonium hydroxide. Tetramethylammonium hydroxide, tetraethyl-ammonium hydroxide, tetrapropylammonium hydroxide and tetrabutylammonium hydroxide are particularly preferred. Tetramethylammonium hydroxide is most particularly preferably used.

It is, of course, also possible to use the bases in mixtures with each other. The most favourable mix ratio in each case may easily be determined by corresponding preliminary trials.

It is also possible to use the inorganic bases in combination with phase transfer catalysts. Suitable phase transfer catalysts are described, for example, in W E Keller, Fluka-Kompendium, Vol. 1, 2, 3, Georg Thieme Verlag publishers, Stuttgart 1986, 1987, 1992. The above-mentioned bases may be used, for example, with crown ethers, such as 18-crown-6 or quaternary ammonium compounds.

The bases to be used according to the invention may have a water content of up to 6 mols of water, preferably up to 3 mols of water, particularly preferably up to 2.5 mols of water, related to one mol of base. Generally speaking a higher water content diminishes the yields.

The bases according to the invention may be added to the reaction mixture in solid form, as melt or as solution or mixture, e.g. in nitrobenzene or in an aprotic solvent or in a mixture of nitrobenzene and one or more aprotic solvents.

The bases are used in a quantity of 0.01 to 3, preferably 0.1 to 2, particularly 0.3 to 1.5 equivalents per mol of nitrobenzene.

Aromatic hydrocarbons with 6 to 20 carbon atoms, linear or cyclic ethers with up to 5 oxygen atoms and 2 to 16 carbon atoms, aromatic halogenated hydrocarbons with 6 to 20 carbon atoms and amides with 1 to 10 carbon atoms may be considered as inert aprotic solvents. The solvents mentioned may, of course, be used in a mixture with each other. The following may be mentioned in particular as suitable solvents: benzene, toluene, xylene, tert.-butylmethylether, tert.-amylmethylether, diisopropylether, diethylene glycol dimethylether, glycol dimethylether, dioxane, tetrahydrofuran, diamylether, chlorobenzene, dichlorobenzene, dimethylformamide, dimethylacetamide and N-methylpyrolidinone. Toluene, xylene, glycol dimethylether, tert.-butylmethylether, diisopropylether, diethylene glycol dimethylether, particularly tert.-butylmethylether and toluene, are preferably used. The quantity of solvent is not critical to the process according to the invention. The most suitable quantity may also easily be determined by corresponding preliminary trials. The quantity of solvent depends in particular on the reaction temperature and on the nature and quantity of the bases and catalysts used. Conventionally the solvents are used in quantities of 1 to 99 wt. %, preferably 5 to 95 wt. %, particularly preferably 15 to 90 wt. %, related to the total quantity of the reaction mixture.

Virtually all heterogeneous catalysts which are known for hydrogenation reactions are suitable as heterogeneous catalysts for the process according to the invention. The catalysts according to the invention comprise metals of the 8–10 group of the periodic system (according to IUPAC, new) or copper and/or chromium on suitable support with a metal content of 0.01 to 50 wt. %, preferably 0.1 to 10 wt. %, related to the total weight of the catalyst. Catalysts which contain one or more of the above-mentioned metals may be used according to the invention. Where several elements are present the weight contents quoted apply to the sum of the individual contents. Preferred metals are platinum, palladium and rhodium in particular, with platinum and palladium being particularly preferred. Further preferred catalysts are Raney nickel and supported nickel catalysts.

The above-mentioned metals or their compounds may also be used according to the invention in pure form as solids. Palladium and platinum black may be quoted as examples of a metal in pure form.

The catalysts according to the invention may be produced according to the most varied methods which are known to the person skilled in the art. Solutions of one or more of the quoted metal compounds may be applied to the catalyst support to be used according to the invention by soaking, adsorption, dipping, spraying, impregnation and ion exchange for example. Further elements may be added to the catalyst in known manner. It is also possible to fix one or more of the quoted metals onto the support by precipitation with a base. Alkali(ne earth) metal hydroxides may be considered as base for example. One or more metals may be applied to the support both in any sequence one after the other and simultaneously. A specific embodiment of the invention involves applying the metal by precipitation of a metal halide or a metal halide complex compound with a suitable base and reduction of the metal compound to the metal. When producing the supports by means of a sol/gel process, in one embodiment solutions of one or more of the quoted metal compounds may already be added to the sol in a manner known to the person skilled in the art.

Suitable materials for use according to the invention as catalyst supports are all technically conventional catalyst supports based on carbon, elemental oxides, elemental carbides or elemental salts in various forms of use. Examples of supports containing carbon are coke, graphite, carbon black or activated charcoals. Examples of elemental oxide catalyst supports are $SiO_2$ (natural or synthetic silica, quartz), $Al_2O_3$ ($\alpha$-, $\gamma$-$Al_2O_3$), aluminas, natural and synthetic aluminosilicates (zeolites), phyllosilicates such as bentonite and montmorillonite, $TiO_2$ (rutile, anatase), $ZrO_2$, MgO or ZnO. Examples of elemental carbides and salts are SiO, $AlPO_4$, $BaSO_4$, $CaCO_3$. In principle, both synthetic materials and supports from natural sources, such as pumice, kaolin, active earths, bauxite, bentonite, diatomaceous earth, asbestos or zeolites, may be used.

Further usable supports for the catalysts which can be used according to the invention are elemental mixed oxides and oxide hydrates of elements of groups 2 to 16 of the periodic system as well as the rare earth metals (atomic numbers 58 to 71), preferably from among the elements Al, Si, Ti, Zr, Zn, Mg, Ca, Zn, Nb and Ce, which may be produced, inter alia, via mechanical mixtures, common precipitations of salts or via cogels of salts and/or alkoxides, as is known to the person skilled in the art.

The supports may be used both in the sense of chemically uniform pure substances and in a mixture. Materials in both lump and powder form are suitable as catalyst supports for use according to the invention. Where the support catalyst is arranged as fixed bed, the support is preferably used as moulded bodies, e.g. as balls, cylinders, small rods, hollow cylinders, rings etc. Alternatively, catalyst supports may be further modified by extrusion, pelletizing, optionally with admixture of further catalyst supports or binders, such as $SiO_2$ or $Al_2O_3$, and calcining. The internal surface of the supports (BET surface) is 1 to 2,000 $m^2/g$, preferably 10 to 1,600 $m^2/g$, most particularly preferably 20 to 1,500 $m^2/g$. Preparation and further processing of the catalyst supports used according to the invention are well known to the person skilled in the art and are the prior art.

Activated charcoals and materials containing Si, Al, Zr and Ti are preferably used as support materials, activated charcoal and supports containing silicon and aluminum are particularly preferred.

In discontinuous process variants, the catalysts according to the invention may be used in quantities of 0.01 to 20 wt. % related to nitrobenzene used, preferably in quantities of 0.01 to 10 wt. %. When the reaction is conducted in a continuous manner, such as in a stirred-tank reactor with a pulverulent catalyst or in the trickle phase on the fixed bed catalyst, loads of 0.01 to 500 g of nitrobenzene per g of catalyst and hour may be used. Loads of 0.02 to 300 g of nitrobenzene per g of catalyst and hour are preferred.

The reaction temperatures in the process according to the invention are preferably 0 to 200° C., particularly 40 to 150° C.; the pressures (hydrogen pressure) are 0.1 to 150 bars, particularly 0.5 to 70 bars, most particularly preferably 1 to 50 bars.

It is possible to conduct the reaction at a constant temperature and at constant hydrogen pressure; hydrogen pressure and temperature may, however, also be changed in the course of the reaction and/or be different in different reactors. When the reaction is discontinuous, nitrobenzene, catalyst, solvent and base may be introduced into the reactor in any sequence. The hydrogen supply may be interrupted after a certain quantity has been supplied, and optionally continued again later.

Examples of continuous process variants are hydrogenation in the liquid phase with a pulverulent suspended catalyst (slurry), hydrogenation in the trickle phase on the fixed bed catalyst or hydrogenation with a suspended catalyst in a bubble column. The reaction may be conducted in the apparatus known to the person skilled in the art for contacting solid, liquid and gaseous phases. Stirred-tank reactors, recirculation reactors, bus reactors, bubble columns operated in concurrent or countercurrent or trickle-phase reactors or cascades of these reactors may be considered in particular, wherein the different reactor types may also occur in a cascade at the same time.

If the catalyst is used as powder in the liquid phase, to mix the reaction components the agitated tanks to be used are equipped with agitators which can be used for this purpose. The use of blade, MIG, propeller, anchor or aerator agitators is possible.

It is particularly surprising that 4-aminodiphenylamine can be produced in technically good yields (>20% of the theory) in the process according to the invention starting with nitrobenzene in a catalytic hydrogenation reaction. This is all the more surprising since it has not hitherto been possible successfully to obtain 4-aminodiphenylamine in appreciable quantities by catalytic hydrogenation of nitrobenzene. It is in fact known that aniline, azoxybenzene, azobenzene and hydrazobenzene are obtained in particular in the catalytic hydrogenation of nitrobenzene (see for example Ullmann 5th ed., vol. A2, 1985, pp. 303–311; S. C. Karwa, Ind. Eng. Chem. Res. 27, 22 (1988); J Wisniak, Ind. Eng. Chem. Res. 1984, 23, 44–50; U.S. Pat. No. 5,420,354). Only with the aid of the process according to the invention is success achieved, as already described, in specifically obtaining 4-aminodiphenylamine in technically interesting yields.

Furthermore, substances occurring in the process according to the invention are intermediate products of the hydrogenation of nitrobenzene to aniline and can be converted without residues into aniline, which is also a valuable starting product for the synthesis of many industrial end products.

EXAMPLES

In the examples below, the reaction products were analyzed by gas chromatography (Permabond SE52-DF-0.25;

25 m×0.32 mm ID) with the internal standard methyl stearate and/or by means of quantitative HPLC. The conversion of nitrobenzene was complete in all the experiments described. Preparation and sample preparation were carried out under nitrogen. The quoted hydrogenation pressures in the autoclave were manually adjusted where there was a pressure drop due to the reaction.

The tetramethylammonium hydroxide hydrates (TMAOH .x$H_2O$) were produced as follows: common commercial pentaydrate (Messrs. Aldrich) or 25% aqueous solution (Messrs. Aldrich) were heated at 80° C. in the water jet vacuum and water extracted thereafter in the pump vacuum or the desiccator over phosphorus pentoxide. The water content achieved was determined by acid titration. The water content of the material used in each case is specified in the batches.

Producing Catalysts A, B, C

Catalyst A (Pt Catalysts)

The support material was heated in the muffle furnace for 2 hours at 350° C. and transferred to a 250 ml flask. A dilute aqueous solution of $H_2PtCl_6$ (produced by diluting an aqueous $H_2PtCl_6$ solution with 25% platinum content) was added to the support material on the rotary evaporator. The quantity of water had been selected so that it was completely absorbed by the support ("incipient wetness"). The majority of the water was then distilled off in vacuo at 60° C., the catalyst dried for 16 hours at 120° C. at a pressure <1 mbar and reduced for 24 hours in a stream of 10 vol. % of hydrogen in nitrogen at 300° C. The Pt content was determined by elementary analysis.

content 25%) in 2.66 g of conc. HCl and 36.3 g of distilled $H_2O$ until the liquid was completely absorbed. The catalyst was then dried for five minutes at 50° C. in the vortex, and reduced for 24 hours at 375° C. in a stream of 10 vol. % of hydrogen in nitrogen.

A) Comparative Examples

The comparative examples demonstrate that conversions in protic solvents do not lead to 4-ADPA to a significant extent:

Comparative Example 1

Conversion in Alcoholic Solution 960 ml of ethanol, 63.6 g of TMAOH . 2.0 $H_2O$, 132.0 g of nitrobenzene (1.1 mol) and 4.8 g of Pt/C catalyst B were placed in the nitrogen-flushed autoclave. Accompanied by agitation and cooling, 5 bars hydrogen pressure were applied and hydrogenation took place for 3 hours 45 minutes. The reaction mixture was then filtered and the ethanol extracted on the rotary evaporator at 70° C. max and a slight vacuum.

The reduced reaction mixture was mixed with 500 ml of toluene in a separating funnel and extracted three times with 1000 ml of distilled water. The organic phase was rotated in vacuo and analyzed. 4-ADPA content: <1 g.

Comparative Example 2

Conversion in Aqueous Solution

A solution of 90 g of tetramethylammonium hydroxide (1 mol TMAOH) in 960 ml of water was placed in a nitrogen-flushed autoclave together with 132.0 g of nitrobenzene (1.1

| Ex. No | Type | Support | BET $m_2/g$ | Support (g) | "Pt" | "$H_2O$" | "Pt %" |
|---|---|---|---|---|---|---|---|
| A1 | $SiO_2$ | Grace Type 432 | 320 | 50.0 | 2.02 | 90.0 | 0.84 |
| A2 | $TiO_2$ | Degussa P 25 | 50 | 30.8 | 1.22 | 93.5 | 1.04 |
| A3 | $ZrO_2$ | Degussa VP $ZrO_2$ | 40 | 28.8 | 1.19 | 60.7 | 1.05 |
| A4 | $Al_2O_3$ | Rhone-Poulenc SPH509 | 335 | 30.0 | 1.23 | 71.0 | 0.96 |
| A5 | $Al_2O_3/SiO_2$ (1.2% Al) | Grace Type III/10 | 345 | 30.2 | 1.23 | 86.4 | 1.03 |
| A6 | $SiO_2/ZrO_2$ (3.9% Zr) | Grace SP2-8402.01 | 306 | 50.0 | 2.08 | 158.0 | 0.98 |

"Pt": quantity of $H_2PtCl_6$ solution (25% Pt content);
"$H_2O$": quantity of water added;
Pt %: platinum content of finished catalyst in wt. %.

Catalyst B (Pt/Activated Charcoal)

475 g of activated charcoal (Norit-B-Supra, Messrs. Norit) were suspended in 2600 ml of deionized water, the mixture heated to 50° C. and mixed with a solution of 87.5 g of sodium formiate in 400 ml of deionized water. In 30 minutes a mixture of 100 g of an $H_2PtCl_6$ solution (25 wt. % Pt) and 400 ml of deionized water was dripped in and agitated further for an hour at 50° C. The catalyst was then extracted, washed and dried in vacuo.

Catalyst C (Rh/Pd/Pt Catalyst)

100 g of γ-$Al_2O_3$ balls (SPH501, Rhone Poulenc) were impregnated with a solution of 0.421 g of $PdCl_2$, 0.674 g of $RhCl_3×4 H_2O$ and 2.02 g of an aqueous $H_2PtCl_6$ solution (Pt mol) and 4.8 g of Pt/C (catalyst B). Hydrogenation took place for 370 minutes with 4 bars hydrogen, accompanied by agitation and at 80° C. The mixture was then cooled to 50° C., filtered in an atmosphere of nitrogen and mixed with 1000 ml of toluene. The mixture was transferred to a separating funnel, shaken and the phases were separated. After phase separation the organic phase was extracted a further two times with 1000 ml of water in each case. The organic phase was rotated in vacuo at 70° C. max. The residue was weighed out and analyzed: it contained no 4-ADPA.

B) Influence of Solvent

The following experiments demonstrate the diversity of aprotic solvents which may be used.

Example 1 (tert.-butylmethylether)

960 ml of tert.-butylmethylether, 127.5 g of TMAOH . 2.0 $H_2O$ (1.0 mol), 132 g of nitrobenzene (1.1 mol) and 2.4 g of Pd/C catalyst (5% Pd/Powder Carbon S-95 386, E169 Mallinckrodt) were placed in a nitrogen-flushed autoclave. Hydrogenation took place for 9 hours at 80° C. with 5 bars hydrogen accompanied by agitation. Cooling to 50° C. then took place and the reaction mixture was filtered in an atmosphere of nitrogen. The procedure was the same with the washing water with which the autoclave had been rinsed out. The filtrates were combined in a separating funnel and shaken. After phase separation the organic phase was extracted a further two times with 1000 ml of distilled water in each case. The solvent was distilled off and the residue subjected to vacuum distillation. The fraction which distilled over at 11 to 12 mbars and 160 to 166° C. contained 23.1 g of 4-ADPA (selectivity: 22.8%).

Example 2: (toluene)

960 ml of toluene, 127.0 g of TMAOH . 2.15 $H_2O$ (0.98 mol), 132.0 g of nitro-benzene (1.1 mol) and 4.8 g of Pt/C catalyst B were placed in a nitrogen-flushed autoclave. Hydrogenation took place for 2 hours at 80° C. with 5 bars hydrogen accompanied by agitation. Cooling to 50° C. then took place. The reaction mixture was filtered in an atmosphere of nitrogen. The procedure was the same with the washing water (approx. 2000 ml) with which the autoclave had been rinsed out. The filtrates were combined in a separating funnel, 500 ml of toluene and NaCl added and shaken. The organic phase was extracted a further two times with 1000 ml of distilled water in each case and rotated in vacuo at 70° C. max. The residue was ground in a mortar and distilled at a vacuum <1 mbar. A product distilled over at 136° C. to 157° C. According to GC analysis the distillate contained 11.5 g of 4-ADPA (selectivity: 11.4%).

Example 3 (tert.-butylmethylether)

960 ml of tert.-butylmethylether, 128.0 g of TMAOH . 2.15 $H_2O$ (0.98 mol), 132 g of nitrobenzene (1.1 mol), 4.8 g of Pt/C catalyst B were placed in the nitrogen-flushed autoclave. Hydrogenation took place for 4 hours 40 minutes at 80° C. with 5 bars hydrogen accompanied by agitation (800 rpm). The reaction mixture was then cooled to 50° C. and filtered in an atmosphere of nitrogen. The procedure was the same with the washing water (approx. 2000 ml) with which the autoclave had been rinsed out. The filtrates were combined in a separating funnel and shaken. The organic phase was extracted a further two times with 1000 ml of distilled water in each case. The first aqueous phase was extracted with 500 ml of toluene. The organic phases were combined and analyzed by GC. Yield: 15.8 g of 4-ADPA (selectivity: 15.6%).

Example 4 (diisopropylether)

960 ml of diisopropylether, 125.4 g of TMAOH . 1.9 $H_2O$ (1.0 mol), 132 g of nitrobenzene (1.1 mol) and 4.8 g of Pd/C catalyst (5% Pd/C catalyst from Example 1) were placed in a nitrogen-flushed autoclave and tempered to 80° C. Hydrogenation took place for 10.5 hours at 80° C. with 5 bars hydrogen accompanied by agitation (800 rpm). Cooling to 50° C. then took place. The mixture was dissolved out of the autoclave with 2 l of water and approx. 800 ml of toluene and filtered off in an atmosphere of nitrogen. The combined filtrates were then shaken in the separating funnel. The organic phase was extracted a further two times with 1000 ml of distilled water in each case. The organic phase was analyzed by GC and HPLC. Yield: 17.8 g of 4-ADPA (selectivity: 17.6%).

Example 5 (tert.-butylmethylether/toluene)

960 ml of tert.-butylmethylether/toluene, 1:1, (V:V), 127.0 g of TMAOH . 2.0 $H_2O$ (1.0 mol), 132.0 g of nitrobenzene (1.1 mol) and 2.4 g of Pd/C catalyst (5% Pd/C catalyst from Example 1) were placed in the nitrogen-flushed autoclave. Hydrogenation took place for 5 hours 15 minutes at 80° C. with 5 bars hydrogen.

The reaction mixture was cooled to 50° C. and filtered in an atmosphere of nitrogen. The procedure was the same with 2 l of washing water with which the autoclave had been rinsed out. The filtrates were combined and shaken in a separating funnel. After phase separation the organic phase was extracted a further two times with 1000 ml of distilled water in each case. The organic phase was analyzed by GC and HPLC. Yield: 16.0 g of 4-ADPA (selectivity: 15.9%).

Example 6 (diglyme)

960 ml of diethyleneglycol dimethylether, 127.5 g of TMAOH . 2.0 $H_2O$ (1.0 mol), 132.0 g of nitrobenzene (1.1 mol) and 2.4 g of Pd/C catalyst (5% Pd/C catalyst from Example 1) were placed in a nitrogen-flushed autoclave. Hydrogenation took place for 3 hours 40 minutes at 80° C. with 5 bars hydrogen. The reaction mixture and 2 l of washing water with which the autoclave had been rinsed out were combined, mixed with 1000 ml of toluene, shaken and filtered in an atmosphere of nitrogen. The filtrate was shaken in a separating funnel. After phase separation the organic phase was extracted a further two times with 1000 ml of distilled water in each case. The organic phase was analyzed by GC and HPLC. Yield: 12.1 g of 4-ADPA (selectivity: 11.9%).

Example 7 (tert.-amylmethylether)

960 ml of tert.-amylmethylether, 127.5 g of TMAOH. 2.0 $H_2O$ (1.0 mol), 132.0 g of nitrobenzene (1.1 mol) and 2.4 g of Pd/C catalyst (5% Pd/C catalyst from Example 1) were placed in a nitrogen-flushed autoclave. Hydrogenation took place for 8 hours 30 minutes at 80° C. with 5 bars hydrogen. The reaction mixture was filtered in an atmosphere of nitrogen. The procedure was the same with the washing water with which the autoclave had been rinsed out. The filtrates were combined in a separating funnel and shaken. The separated organic phase was extracted a further two times with 1000 ml of distilled water in each case. The organic phase was analyzed by GC and HPLC. Yield: 14.2 g of 4-ADPA (selectivity: 14.0%).

C) Base Variation

The following experiments demonstrate that different quantities of base with different quantities of hydrate are suitable.

Example 8 (1 mol of TMAOH-dihydrate)

960 ml of tert.-butylmethylether, 127.5 g of TMAOH . 2.0 $H_2O$ (1.0 mol), 132 g of nitrobenzene (1.1 mol) and 2.4 g of Pd/C catalyst (5% Pd/C catalyst from Example 1) were placed in a nitrogen-flushed autoclave. Hydrogenation took place for 7 hours 10 minutes at 80° C. with 5 bars hydrogen. The reaction mixture was filtered in an atmosphere of nitrogen. The procedure was the same with the washing water with which the autoclave had been rinsed out. The filtrates were combined in a separating funnel and shaken. After phase separation the organic phase was extracted a further two times with 1000 ml of distilled water in each case. The organic phase was analyzed by GC and HPLC. Yield: 17.2 g of 4-ADPA (selectivity: 17.0%).

Example 9 (1/2 mol of TMAOH-dihydrate)

960 ml of tert.-butylmethylether, 63.5 g of TMAOH . 2.0 $H_2O$ (0.5 mol), 132 g of nitrobenzene (1.1 mol) and 2.4 g of Pd/C catalyst (5% Pd/C catalyst from Example 1) were placed in a nitrogen-flushed autoclave. Hydrogenation took place for 6 hours at 80° C. with 5 bars hydrogen. The reaction mixture was filtered in an atmosphere of nitrogen. The procedure was the same with the washing water with which the autoclave had been rinsed out. The filtrates were combined and shaken in a separating funnel. After phase separation the organic phase was extracted a further two times with 1000 ml of distilled water in each case. The organic phase was analyzed by GC and HPLC. Yield: 10.5 g of 4-ADPA (selectivity: 10.4%).

Example 10 (2 mols of TMAOH-dihydrate)

960 ml of tert.-butylmethylether, 255.0 g of TMAOH . 2.0 $H_2O$ (2.0 mol of base), 132.0 g of nitrobenzene (1.1 mol) and 2.4 g of Pd/C catalyst (5% Pd/C catalyst from Example 1) were placed in a nitrogen-flushed autoclave. Hydrogenation took place for 7 hours 30 minutes at 80° C. with 5 bars hydrogen. Undissolved solid contained in the reaction mixture was dissolved with 1000 ml of water and 300 ml of toluene. The solution, and the washing water with which the autoclave had been rinsed out, were then filtered in an atmosphere of nitrogen. The filtrate was shaken in a separating funnel. After phase separation the organic phase was extracted a further two times with 1000 ml of distilled water in each case. The organic phase was analyzed by GC and HPLC. Yield: 18.07 g of 4-ADPA (selectivity: 17.8%).

Example 11 (1 mol of TMAOH-dihydrate+1 mol of water)

960 ml of tert.-butylmethylether, 127.5 g of TMAOH . 2.0 $H_2O$ (1.0 mol), 132 g of nitrobenzene (1.1 mol), 18 g of distilled water and 2.4 g of Pd/C catalyst (5% A-Pd/C catalyst from Example 1) were placed in a nitrogen-flushed autoclave. 5 bars hydrogen pressure were applied accompanied by agitation. Hydrogenation took place for 10 hours 30 minutes at 80° C. with 5 bars hydrogen. The reaction mixture was filtered in an atmosphere of nitrogen. The procedure was the same with the washing water with which the autoclave had been rinsed out. The filtrates were combined and shaken in a separating funnel. After phase separation the organic phase was extracted a further two times with 1000 ml of distilled water in each case. The organic phase was analyzed by GC and TPLC. Yield: 10.4 g of 4-ADPA (selectivity: 10.3%).

Example 12 (1 mol of TMAOH-1.5 $H_2O$)

960 ml of tert.-butylmethylether, 118.2 g of TMAOH . 1.5 $H_2O$ (1.0 mol), 132 g of nitrobenzene (1.1 mol) and 2.4 g of Pd/C catalyst (5% Pd/C catalyst from Example 1) were placed in a nitrogen-flushed autoclave. 5 bars hydrogen pressure were applied accompanied by agitation. Hydrogenation took place for 6 hours 30 minutes at 80° C. with 5 bars hydrogen. The reaction mixture was filtered in an atmosphere of nitrogen. The procedure was the same with the washing water with which the autoclave had been rinsed out. The filtrates were combined and shaken in a separating funnel. After phase separation the organic phase was extracted a further two times with 1000 ml of distilled water in each case. The organic phase was analyzed by GC and HPLC. Yield: 15.0 g of 4-ADPA (selectivity: 14.8%).

D) Higher Concentrations

Example 13

480 ml of tert.-butylmethylether, 127.5 g of TMAOH . 1.5 $H_2O$ (1.0 mol), 132.0 g of nitrobenzene (1.1 mol) and 4.8 g of Pd/C catalyst (5% Pd/C catalyst from Example 1) were placed in a nitrogen-flushed autoclave. 5 bars hydrogen pressure were applied accompanied by agitation. Hydrogenation took place for 4 hours 45 minutes at 80° C. with 5 bars hydrogen. The reaction mixture was filtered in an atmosphere of nitrogen. The procedure was the same with the washing water with which the autoclave had been rinsed out. The filtrates were combined and shaken in a separating funnel. After phase separation the organic phase was extracted a further two times with 1000 ml of distilled water in each case. The organic phase was analyzed by GC and HPLC. Yield: 18.0 g of 4-ADPA (selectivity: 17.8%).

E) Temperature and Pressure Variation

The following examples demonstrate temperatures and pressures which can be used.

Example 14 (60° C.)

820 ml of toluene, 110 g of TMAOH . 2.1 $H_2O$ (0.85 mol), 113 g of nitrobenzene (0.92 mol) and 4.1 g of Pt/C catalyst B were placed in a nitrogen-flushed autoclave. Hydrogenation took place for 6 hours with 5 bars hydrogen. The reaction mixture was then cooled to 50° C. and filtered under an atmosphere of nitrogen. The procedure was the same with the washing water with which the autoclave had been rinsed out. The filtrates were combined in a separating funnel and shaken. After phase separation the organic phase was extracted a further two times with 1000 ml of distilled water in each case. The organic phases were combined and analyzed by GC. Yield: 8.2 g of 4-ADPA (selectivity: 8.1%).

Example 15 (100° C.)

960 ml of toluene, 128.9 g of TMAOH . 2.1 $H_2O$ (1.0 mol), 132.0 g of nitro-benzene (1.1 mol) and 4.8 g of Pt/C catalyst B were placed in a nitrogen-flushed autoclave. Hydrogenation took place for 1 hour 55 minutes at 100° C. with 5 bars hydrogen. The reaction mixture was filtered in an atmosphere of nitrogen together with the washing water, mixed with 500 ml of toluene and shaken in the separating funnel. The organic phase was extracted a further two times with 1000 ml of distilled water in each case. The organic phase was analyzed by GC and HPLC. Yield: 14.4 g of 4-ADPA (selectivity: 14.2%).

Example 16: (100° C.)

960 ml of tert.-butylmethylether, 127.5 g of TMAOH. 2.0 $H_2O$ (1.0 mol), 132.0 g of nitrobenzene (1.1 mol) and 2.4 g of Pd/C catalyst (5% Pd/C catalyst from Example 1) were placed in a nitrogen-flushed autoclave. Hydrogenation took place for 5 hours [at 80° C.] with 5 bars hydrogen. The autoclave was washed out with 2 l of water and the reaction mixture was filtered with the washing water and 200 ml of toluene in an atmosphere of nitrogen. The separated organic phase was extracted a further two times with 1000 ml of distilled water in each case. The organic phase was analyzed by GC and HPLC. Yield: 16.8 g of 4-ADPA (selectivity: 16.6%).

Example 17: (10 atm)

960 ml of tert.-butylmethylether, 127.5 g of TMAOH. 2.0 $H_2O$ (1.0 mol), 132.0 g of nitrobenzene (1.1 mol) and 1.2 g of Pd/C catalyst (5% Pd/C catalyst from Example 1) were placed in a nitrogen-flushed autoclave. Hydrogenation took place for 12.5 hours at 80° C. with 5 bars hydrogen. The autoclave was washed out with 2 l of water and the reaction mixture was filtered with the washing water and 200 ml of toluene in an atmosphere of nitrogen. The separated organic phase was extracted a further two times with 1000 ml of distilled water in each case. The organic phase was analyzed by GC and HPLC. Yield: 16.8 g of 4-ADPA (selectivity: 16.6%).

Example 18: (50 atm)

This Experiment also Demonstrates That High Concentrations are also Suitable 246 g of tert.-butylmethylether, 250.7 g of TMAOH . 1.9 $H_2O$ (2.0 mol), 246.0 g of nitrobenzene and 4.8 g of Pd/C catalyst (5% Pd/C catalyst from Example 1) were placed in a nitrogen-flushed autoclave. Hydrogenation took place for 24 hours at 80° C. with 5 bars hydrogen. After addition of 400 ml of toluene the batch was filtered accompanied by nitrogen, together with the washing water with which the autoclave had been rinsed out in an atmosphere of nitrogen. The filtrates were combined in a separating funnel and shaken. The separated organic phase was extracted a further two times with 1000 ml of distilled water in each case and analyzed by GC. Yield: 28.8 g of 4-ADPA (selectivity: 14.2%).

F) Variation of Catalysts

The following examples demonstrate the use of different catalysts and quantities of catalyst. Furthermore, they demonstrate the possibility of conducting the reaction at ambient pressure.

Examples 19–35 (Ambient Pressure Hydrogenations)

75 ml of diethyleneglycol dimethylether or 48 g of toluene, 7.03 g of TMAOH . 2.0 $H_2O$, and the pulverulent catalyst, were placed in a nitrogen-flushed 250 ml flat ground-glass pot with aeration agitator and heated to 80° C. After this temperature had been reached the nitrogen was replaced by a hydrogen stream of 25 l/hr at ambient pressure and 6.77 g of nitrobenzene were added at the same time. After 120 minutes a sample was taken, filtered, neutralized with acetic acid and analyzed by quantitative gas chromatography. The conversion of nitrobenzene was complete in all experiments. The results are shown in the Table below.

| Example | Catalyst | Amount of catalyst (g) | LM | S |
|---|---|---|---|---|
| 19 | 5% Pd/C, Engelhard, code 3230, lot 2942 | 0.2 | T | 25.8 |

-continued

| Example | Catalyst | Amount of catalyst (g) | LM | S |
|---|---|---|---|---|
| 20 | 5% Pd/C, Engelhard, code 3230, lot 2942 | 0.1 | T | 23.8 |
| 21 | 5% Pd/C (Aldrich) | 0.5 | D | 14.8 |
| 22 | 10% Pd/C (Aldrich) | 0.25 | D | 12.2 |
| 23 | 5% Pt/C, Mallinkrodt, S-95-38b, E169 | 0.5 | D | 18.1 |
| 24 | Catalyst B | 0.25 | D | 24.7 |
| 25 | Catalyst B | 0.5 | T | 17.6 |
| 26 | 5% Rh/$Al_2O_3$ (Aldrich) | 0.5 | D | 17.0 |
| 27 | 5% Pd/$BaSO_4$ (Aldrich) | 0.5 | D | 17.8 |
| 28 | 5% Pd/$BaCO_3$ (Aldrich) | 0.5 | D | 14.4 |
| 29 | Catalyst A1 | 2.3 | D | 22.4 |
| 30 | Catalyst A2 | 2.4 | D | 19.1 |
| 31 | Catalyst A3 | 2.6 | D | 21.8 |
| 32 | Catalyst A4 | 2.6 | D | 23.6 |
| 33 | Catalyst A5 | 2.4 | D | 16.7 |
| 34 | Catalyst A6 | 1.0 | D | 23.5 |
| 35 | Catalyst C | 2.1 | D | 20.8 |

LM: solvent. D: diglyme. T: toluene. S: selectivity to 4-ADPA in mol % related to nitrobenzene.

Example 36 (Rhodium/C Catalyst, Pressure Reaction)

960 ml of tert.-butylmethylether, 127.5 g of TMAOH . 2.0 $H_2O$ (1.0 mol), 132 g of nitrobenzene (1.1 mol) and 2.4 g (5% Rh/C, Merck; order No. 818 851) were placed in a nitrogen-flushed autoclave. Hydrogenation took place for 6 hours at 80° C. with 5 bars hydrogen. The reaction mixture was filtered in an atmosphere of nitrogen. The procedure was the same with the washing water with which the autoclave had been rinsed out. The filtrates were combined in a separating funnel and shaken. After phase separation the organic phase was extracted a further two times with 1000 ml of distilled water in each case. The organic phase was analyzed by GC and HPLC. Yield: 13.6 g of 4-ADPA (selectivity: 13.4%).

We claim:

1. A process for producing 4-aminodiphenylamine, the process comprising hydrogenating nitrobenzene with hydrogen in a reaction mixture consisting essentially of at least one base containing hydroxide and/or oxide groups and at least one heterogeneous catalyst and in the presence of inert aprotic solvent at temperatures of 0 to 200° C. and pressures of 0.1 to 150 bars.

2. A process according to claim 1, wherein the hydrogenation is carried out at temperatures of 40 to 150° C. and pressures of 0.5 to 70 bars.

3. A process according to claim 1, wherein the bases containing hydroxide and/or oxide groups are selected from the group consisting of alkali hydroxides, alkaline earth metal oxides, alkaline earth metal hydroxides, alkaline earth metal oxides, the corresponding hydroxides and oxides of elements 58 to 71 of the periodic system of elements (IUPAC, new) and quaternary alkylammonium hydroxides.

4. A process according to claim 1, wherein the base is used in quantities of 0.01 to 3 equivalents per mol of nitrobenzene.

5. A process according to claim 1, wherein the aprotic solvent is selected from aromatic hydrocarbons with 6 to 20 carbon atoms, linear or cyclic ethers with up to 5 oxygen atoms and 2 to 16 carbon atoms, aromatic halogenated hydrocarbons with 6 to 20 carbon atoms, and amides with 1 to 10 carbon atoms.

6. A process according to claim 1, wherein the inert aprotic solvents are used in quantities of 1 to 99 wt. %, related to the total quantity of the reaction mixture.

7. A process according to claim 1, wherein metals of the 8–10 Group of the periodic system (IUPAC, new) or copper and/or chromium, optionally applied to a catalyst support, are used as heterogeneous catalysts.

8. A process according to claim 1, which is carried out discontinuously using the catalyst in quantities of 0.01 to 20 wt. %, related to the nitrobenzene.

9. A process as claimed in claim 1, which is carried out continuously using 0.01 to 500 g. of nitrobenzene per gram of catalyst and per hour.

* * * * *